US010022312B2

(12) United States Patent
Massoni et al.

(10) Patent No.: US 10,022,312 B2
(45) Date of Patent: *Jul. 17, 2018

(54) GRADUAL HAIRCOLOR COMPOSITIONS AND METHODS OF USING THE SAME

(71) Applicant: Combe Incorporated, White Plains, NY (US)

(72) Inventors: Jack T. Massoni, New Fairfield, CT (US); Padmaja Prem, Saddle Brook, NJ (US)

(73) Assignee: COMBE INCORPORATED, White Plains, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/264,979

(22) Filed: Sep. 14, 2016

(65) Prior Publication Data

US 2017/0000708 A1    Jan. 5, 2017

Related U.S. Application Data

(63) Continuation of application No. 14/992,098, filed on Jan. 11, 2016, now Pat. No. 9,474,704, which is a continuation of application No. 14/166,963, filed on Jan. 29, 2014, now Pat. No. 9,237,993.

(60) Provisional application No. 61/931,174, filed on Jan. 24, 2014.

(51) Int. Cl.
| *A61Q 5/10* | (2006.01) |
| *A61K 8/41* | (2006.01) |
| *A61K 8/22* | (2006.01) |
| *A61Q 5/02* | (2006.01) |
| *A61Q 5/12* | (2006.01) |
| *A61K 8/34* | (2006.01) |
| *A61K 8/46* | (2006.01) |
| *A61K 8/60* | (2006.01) |
| *A61Q 5/00* | (2006.01) |

(52) U.S. Cl.
CPC .............. *A61K 8/415* (2013.01); *A61K 8/22* (2013.01); *A61K 8/347* (2013.01); *A61K 8/463* (2013.01); *A61K 8/466* (2013.01); *A61K 8/602* (2013.01); *A61Q 5/006* (2013.01); *A61Q 5/02* (2013.01); *A61Q 5/10* (2013.01); *A61Q 5/12* (2013.01); *A61K 2800/4324* (2013.01)

(58) Field of Classification Search
CPC ... A61Q 5/10; A61Q 5/02; A61Q 5/12; A61K 8/463; A61K 8/602; A61K 8/466; A61K 8/347; A61K 2800/4324
See application file for complete search history.

(56) References Cited

U.S. PATENT DOCUMENTS

| 3,920,384 | A | | 11/1975 | Feinland et al. |
| 4,054,413 | A | * | 10/1977 | Feinland ............... A61K 8/347 |
| | | | | 8/410 |
| 4,297,098 | A | | 10/1981 | Dasher et al. |
| 4,529,404 | A | | 7/1985 | Feinland et al. |
| 4,662,892 | A | | 5/1987 | Pike |
| 5,096,455 | A | | 3/1992 | Grollier |
| 5,167,669 | A | | 12/1992 | Grollier |
| 5,350,424 | A | | 9/1994 | Shansky |
| 6,537,330 | B1 | | 3/2003 | Hoeffkes et al. |
| 6,818,023 | B2 | | 11/2004 | Hoeffkes et al. |
| 7,060,108 | B2 | | 6/2006 | Morita et al. |
| 7,608,116 | B2 | | 10/2009 | Nicolas-Morgantini et al. |
| 7,758,659 | B2 | | 7/2010 | Massoni |
| 7,947,090 | B2 | | 5/2011 | Massoni |
| 8,716,214 | B2 | | 5/2014 | Dahms et al. |
| 9,237,993 | B2 | * | 1/2016 | Massoni ................. A61K 8/22 |
| 9,358,190 | B2 | | 6/2016 | Kim et al. |
| 9,474,704 | B2 | * | 10/2016 | Massoni ................. A61K 8/22 |
| 2002/0015685 | A1 | | 2/2002 | Pascual et al. |
| 2003/0154561 | A1 | * | 8/2003 | Patel ...................... A61K 8/411 |
| | | | | 8/405 |
| 2004/0158938 | A1 | | 8/2004 | Geary et al. |
| 2004/0158940 | A1 | * | 8/2004 | Wells ....................... A61K 8/03 |
| | | | | 8/406 |
| 2005/0283925 | A1 | | 12/2005 | Glenn et al. |
| 2006/0016024 | A1 | * | 1/2006 | Knuebel ................ A61K 8/411 |
| | | | | 8/405 |
| 2007/0081953 | A1 | | 4/2007 | Dahms |
| 2009/0114237 | A1 | | 5/2009 | Massoni et al. |
| 2009/0320215 | A1 | | 12/2009 | Massoni et al. |

(Continued)

FOREIGN PATENT DOCUMENTS

CN      1424901 A      6/2003
CN    101990406 A      3/2011

(Continued)

OTHER PUBLICATIONS

International Search Report in International Application No. PCT/US2015/012574 (dated Apr. 29, 2015).
Written Opinion in International Application No. PCT/US2015/012574 (dated Apr. 29, 2015).
Bendejacq, D., et al., "Structured Surfactant Systems for High Performance Shampoos," Cosmetics & Toiletries, 125(11), pp. 22-29 (2010).
Ghosh, S., et al., "Why is Sodium Cocoyl Isethionate (SCI) Mild to the Skin Barrier?—An in Vitro Investigation Based on the Relative Sizes of the SCI Micelles and the Skin Aqueous Pores," 58(3) J. Cosmet. Sci. 229-244 (2007).
Office Action in Taiwanese Application No. 104102425 (dated Jan. 25, 2016).
Office Action in Russian Application No. 2016134428 (dated Apr. 26, 2017).

(Continued)

*Primary Examiner* — Eisa B Elhilo
(74) *Attorney, Agent, or Firm* — Fitzpatrick, Cella, Harper & Scinto

(57) ABSTRACT

The disclosure relates to a method for gradually coloring hair comprising the steps of: a) applying an air oxidation haircolor composition to hair; b) removing the air oxidation haircolor composition from the hair directly after application; and c) repeating a set comprising the steps a) and b) in multiple spaced intervals. The air oxidation haircolor composition can include: 1) at least one primary oxidation dye intermediate; 2) at least one aromatic triol; and 3) water.

18 Claims, No Drawings

(56) References Cited

U.S. PATENT DOCUMENTS

| | | |
|---|---|---|
| 2010/0146717 A1 | 6/2010 | Massoni |
| 2010/0170048 A1 | 7/2010 | Koike et al. |
| 2012/0183591 A1 | 7/2012 | Dahms |

FOREIGN PATENT DOCUMENTS

| | | |
|---|---|---|
| EP | 1 062 939 A1 | 12/2000 |
| EP | 1 832 273 A1 | 9/2007 |
| JP | 51-35441 A | 3/1976 |
| JP | 58-55408 A | 4/1983 |
| JP | 3-58916 A | 3/1991 |
| JP | 3-86813 A | 4/1991 |
| JP | 6-279246 A | 10/1994 |
| JP | 7-82120 A | 3/1995 |
| JP | 2001-527031 A | 12/2001 |
| JP | 2002-518424 A | 6/2002 |
| JP | 2003-192548 A | 7/2003 |
| JP | 2006-525282 A | 11/2006 |
| JP | 2010-500349 A | 1/2010 |
| JP | 2012-62250 A | 3/2012 |
| RU | 2232570 C2 | 7/2004 |
| WO | 94/04125 A1 | 3/1994 |
| WO | 97/05857 A1 | 2/1997 |
| WO | 99/33435 A1 | 7/1999 |
| WO | 01/45657 A1 | 6/2001 |
| WO | 2008/020983 A2 | 2/2008 |
| WO | 2013/077072 A1 | 5/2013 |

OTHER PUBLICATIONS

First Office Action in Chinese Application No. 201580004944.9 (dated Mar. 24, 2017).
First Examination Report in Australian Application No. 2015209222 (dated May 5, 2017).
Notice of Reasons for Refusal in Japanese Application No. 2016-548226 (dated Dec. 12, 2016).
First Examination Report in New Zealand Application No. 721983 (dated Feb. 28, 2017).
Communication Pursuant to Article 94(3) EPC in European Application No. 15705133.5 (dated Nov. 10, 2017).
Mintel "Toner Gel Shampoo" Product Sheet (2 pages), Database Accession No. 995159 (Oct. 2008).
Second Office Action in Chinese Application No. 201580004944.9 (dated Dec. 12, 2017).
Decision of Rejection in Japanese Application No. 2016-548226 (dated Jul. 31, 2017).
Examination report No. 2 in Australian Application No. 2015209222 (dated May 2, 2018).
Office Action in Russian Application No. 2016134428 (dated Nov. 23, 2017).
Third Office Action in Chinese Application No. 201580004944.9 (dated May 2, 2018).

\* cited by examiner

GRADUAL HAIRCOLOR COMPOSITIONS AND METHODS OF USING THE SAME

CROSS-REFERENCE TO RELATED APPLICATIONS

This application is a continuation application of U.S. patent application Ser. No. 14/992,098, filed Jan. 11, 2016, which is a continuation application of U.S. patent application Ser. No. 14/166,963, filed Jan. 29, 2014, now U.S. Pat. No. 9,237,993, which claims the benefit of priority from U.S. Provisional Application No. 61/931,174, filed Jan. 24, 2014. The contents of these prior applications are incorporated by reference herein in their entirety.

BACKGROUND

Field

The disclosure relates to air oxidation haircolor compositions and methods of using the same, including a method for gradually coloring hair, a method for simultaneously cleansing and gradually coloring hair, a method for simultaneously conditioning and gradually coloring hair, and a method for cleansing, conditioning and gradually coloring hair.

Related Background Art

Permanent (or oxidation) hair coloring products constitute the majority of hair coloring formulas used in modern times. These products have the ability to change the color of gray or pigmented hair, as they permanently alter the hair's natural coloration. Reapplication occurs as new hair growth becomes noticeable. Oxidation hair dyes are normally sold in the form of a two-component kit. One container comprises an alkaline composition with oxidation dyes and an appropriate vehicle. The other container comprises a developer composition that utilizes an oxidizing agent, usually hydrogen peroxide. The two compositions are mixed immediately prior to application to the hair. The alkaline pH of the resultant mixture causes the hair shaft to swell, allowing the dye precursors to penetrate into the cortex of the hair. These dye precursors are then oxidized and combine to form larger molecules. These larger molecules contain a significant level of conjugated double bonds, hence producing a colored product that is visible from the exterior of the hair. After an appropriate development time during which the composition dwells on the hair, the mixture is rinsed from the hair. The color of the hair is then permanently altered. Depending upon the pH of the mixture and the strength of the developer, these systems can either have the capability to simultaneously lighten the hair's natural pigment and deposit color, or to just deposit color. The so-called "deposit only permanent colors" have played a minor role in retail women's products marketed in the past 30 years, but have a significant share of the professional market. They also make up the majority of men's hair colorants sold today.

Attempts have been made to replace or eliminate the harsh developer portion of oxidation dye products. Several advancements involve the use of enzymes or solutions of chlorites as replacements to hydrogen peroxide. These systems still require two separate components that are mixed immediately prior to application. Although these alternative formulas are milder and reduce damage to the hair, they do not offer any great advantages in relation to improved convenience, messiness, ease of use or color delivery. However, the air oxidation dyes or auto oxidation hair dyes, as they are called, eliminate the need for the addition of a developer and a mixing step. As the name implies, these compositions rely on atmospheric oxygen for color development. No mixing is required. Formulas containing these dyes are conventionally applied to the hair by using leave-in formulations that are removed the following day by traditional cleansing methods. Full color coverage is then permanently imparted.

The first practical applications of this technology are discussed in U.S. Pat. Nos. 3,920,384, 4,054,413, 4,529,404 and 4,297,098. Traditional primary dye intermediates were combined with dye couplers that had a high degree of electron donating groups on the aromatic ring. The most popular of these couplers include: 1,2,4-trihydroxybenzene, 2,4,5-trihydroxytoluene, and pyrogallol. These dye intermediates may be included within a vehicle that contains styling properties and can be delivered from an aerosol can in the form of a foam. The aerosol container also affords an anaerobic environment to preserve the stability and hence efficacy of the formula. The product is then left in the hair until it is removed, generally about one or two days later. Full color coverage is then provided.

However, there have not been any truly successful attempts in finding a means of gradually coloring hair; in other words, a means to gradually develop color build-up on the hair a little at a time upon multiple applications, so that hair coloring is less noticeable day by day to others. Until recently, lead acetate compositions were the only effective means of accomplishing this coloration. These types of products develop and maintain partial gray coverage.

Also, while there are products that can be used to shampoo, thicken, regrow and/or condition and impart a permanent hair color, these products do not accomplish their goal via application of a single composition. For example, these products employ consecutive treatment formulas (see e.g., U.S. Pat. No. 6,758,867) and/or, more specifically, require a shampoo or cleanser with typical oxidation dye intermediates at high pH, which is applied to the hair and removed, followed by a conditioner or, after treatment at an acidic pH, an oxidizer, such as hydrogen peroxide, to develop the color.

SUMMARY

To address the shortcomings of conventional hair coloring products and methods, provided herein are hair coloring compositions incorporating air oxidation dyes that can be used to achieve a gradual (or progressive) change in color of hair and can be regularly and easily included in an individual's daily grooming discipline. Such compositions are used in personal hair and body care products including, but not limited to, shampoos, conditioners, conditioning shampoos, hair thickening and regrowth compositions, body washes, and cleanser compositions in general, wherein the compositions can simultaneously provide their normal daily grooming function and gradually color hair with repeated use.

In particular, a method for gradually coloring hair as disclosed herein can comprise the steps of: a) applying an air oxidation haircolor composition to hair; b) removing the air oxidation haircolor composition from the hair directly after application; and c) repeating a set comprising the steps a) and b) in multiple spaced intervals, wherein the air oxidation haircolor composition comprises: at least one primary oxidation dye intermediate; at least one aromatic triol; and water. In certain embodiments thereof, a primary oxidation dye intermediate content is about 0.01% to about 5% weight by weight of the air oxidation haircolor composition; an aromatic triol content is about 0.01% to about 5% weight by weight of the air oxidation haircolor composition; or may be a conditioner composition and/or a cleanser. In another embodiment: 1) the primary oxidation dye intermediate content of the air oxidation haircolor composition is about 0.1% to about 3% weight by weight of the air oxidation haircolor composition; 2) the aromatic triol content is about 0.1% to about 3% weight by weight of the air oxidation haircolor composition; 3) a water content is about 40% to about 98% weight by weight of the air oxidation haircolor composition; and 4) a cleansing surfactant content is greater than 5% to about 50% weight by weight and/or a conditioning agent content is about 0.5% to about 15% weight by weight of the air oxidation haircolor composition.

An embodiment of the disclosure is a method for simultaneously cleansing and gradually coloring hair comprising the steps of: a) applying an air oxidation haircolor composition to hair; and b) removing the air oxidation haircolor composition from the hair directly after application, wherein the air oxidation haircolor composition is an air oxidation haircolor grooming composition comprising: 1) at least one primary oxidation dye intermediate, where a primary oxidation dye intermediate content is about 0.01% to about 5% weight by weight; 2) at least one aromatic triol, where an aromatic triol content is about 0.01% to about 5% weight by weight; 3) water, where a content is about 40% to about 98% weight by weight; and 4) at least one cleansing surfactant, where a cleansing surfactant content is greater than 5% to about 50% weight by weight.

Another embodiment is a method for simultaneously conditioning and gradually coloring hair comprising the steps of: a) applying an air oxidation haircolor composition to hair; and b) removing the air oxidation haircolor composition from the hair directly after application, wherein the air oxidation haircolor composition is an air oxidation haircolor grooming composition comprising: 1) at least one primary oxidation dye intermediate, where a primary oxidation dye intermediate content is about 0.01% to about 5% weight by weight; 2) at least one aromatic triol, where an aromatic triol content is about 0.01% to about 5% weight by weight; 3) water, where a content is about 40% to about 98% weight by weight; and 4) at least one conditioning agent, where a conditioning agent content is about 0.1% to about 15% weight by weight.

A further embodiment is an air oxidation haircolor shampoo composition comprising: 1) at least one primary oxidation dye intermediate, where a primary oxidation dye intermediate content is about 0.1% to about 3% weight by weight; 2) at least one aromatic triol, where an aromatic triol content is about 0.1% to about 3% weight by weight; 3) water, where a content is about 40% to about 98% weight by weight; and 4) at least one cleansing surfactant, where a cleansing surfactant content is greater than 5% to about 50% weight by weight; wherein the air oxidation haircolor shampoo composition cleanses hair; and wherein the air oxidation haircolor shampoo composition gradually colors hair with repeated use.

A still further embodiment is an air oxidation haircolor conditioner composition comprising: 1) a primary oxidation dye intermediate content of about 0.1% to about 3% weight by weight; 2) an aromatic triol content of about 0.1% to about 3% weight by weight; 3) a water content of about 40% to about 98% weight by weight; and 4) at least one conditioning agent, where a conditioning agent content is about 0.1% to about 15% weight by weight; wherein the air oxidation haircolor conditioner composition conditions the hair; and wherein the air oxidation haircolor conditioner composition gradually colors hair with repeated use.

DETAILED DESCRIPTION

Air oxidation haircolor and air oxidation haircolor grooming (e.g., cleanser and/or conditioner) compositions are disclosed herein that can be used to achieve a gradual (or progressive) change in color of hair and can be regularly and easily included in an individual's daily grooming discipline. Products containing these compositions include, but are not limited to, shampoos, conditioners, hair thickening and regrowth compositions, body washes, and cleanser compositions in general, wherein the compositions can simultaneously provide their normal daily grooming function and gradually color hair. These products are designed to gradually impart color to hair by oxygen activation of dye precursors in the formula when used repeatedly until the desired color is achieved.

An air oxidation haircolor composition or air oxidation haircolor grooming composition as used herein refers to a composition that does not require mixing or contact with a separate oxidant (other than air or atmospheric oxygen) prior, during or after application to hair to color the hair. Thus, the air oxidation haircolor compositions disclosed herein can cover gray and enhance natural pigmented hair without oxidative hair damage.

The air oxidation haircolor composition as disclosed herein that, in addition to coloring hair, can also perform a grooming function, such as cleansing and/or conditioning the hair, can do so without being combined with any additional component (other than atmospheric oxygen or air to develop the color and possibly water) before, during or after application to the hair. That is, it is a single composition (e.g., liquid, cream, gel, emulsion, lotion, foam) that contains ingredients in sufficient amounts to provide both grooming and coloring functionalities in a single application, and it need not be combined with any other composition.

Thus, the air oxidation haircolor composition can be applied from a single container to achieve the intended result with short dwell times. This is different from, and more advantageous than, application of multiple compositions from different containers, which are applied to and combined on the hair, or mixed (or pre-mixed) shortly before being applied to the hair.

Because these air oxidation haircolor compositions use air as the oxidant, they are milder and less damaging to the hair and have better color retention than traditional multi-part systems. The air oxidation haircolor compositions disclosed herein are very efficient dye carriers which allow for unexpectedly quick dye penetration into the hair shaft. This may be accomplished within a minute or two of application, which is a typical use time for many conventional types of grooming products.

In order to achieve fast dwell times and other benefits of the air oxidation haircolor compositions disclosed herein, dye couplers that are used should have a high degree of electron donating groups on the aromatic ring, such as 1,2,4-trihydroxybenzene. Unlike conventional dyes, the air oxidation haircolor composition as disclosed herein can be formulated within the typical pH range expected for the underlying grooming product, which further provides for an improved mild product.

The methods for gradually coloring hair as disclosed herein employ these air oxidation haircolor compositions.

Thus, the air oxidation haircolor compositions disclosed herein may be used as a daily hair care product, in place of one's shampoo, conditioner or cleanser, and can be removed after the same amount of time as the conventional grooming products like which they are formulated to function in addition to coloring hair, even in as little as 1 minute or in as long as 1 hour. The daily use of these compositions gradually increases the color deposit, whereby the consumer can change frequency of use from daily to weekly, or even less frequently, once the desired color is obtained in order to maintain the color. By developing the hair color gradually and then using the formulas to maintain a specific degree of coloration, an added benefit of little to no visible regrowth can be achieved. With conventional full color compositions that are applied monthly, the appearance of regrowth or untreated hair is considered an undesirable effect.

One embodiment is a method for gradually coloring hair comprising the steps of: a) applying an air oxidation haircolor composition to hair; b) removing the air oxidation haircolor composition from the hair directly after application; and c) repeating a set comprising the steps a) and b) in multiple spaced intervals, wherein the air oxidation haircolor composition comprises: 1) at least one primary oxidation dye intermediate; 2) at least one aromatic triol; and 3) water.

Gradually coloring hair, as used herein, refers to providing less than complete coverage with one use of the air oxidation haircolor composition. Preferably, gradually coloring hair is achieving about 30% or less, about 20% or less, about 15% or less, or 10% or less, of color development of one's natural shade with every application. Thus, with gradual coloring, each successive use provides additional coverage, imparts further coloring to the hair, and develops color build-up on the hair. Thus, one air oxidation haircolor composition is able to achieve multiple different shades of one hair color, and with each application to the hair, the shade of that color darkens.

Application of the air oxidation haircolor composition may be achieved by any means known in the art, including, but not limited to, by hand or brush. The air oxidation haircolor composition may be applied to wet or to dry hair, and preferably, to wet hair.

Application and removal in multiple spaced intervals refers to multiple sets of applying to and then removing from the hair the air oxidation haircolor composition to achieve the gradual coloring, i.e., gradual build-up of color on the hair, and the intervals of time between each set of applying and removing may be the same or different, including bi-monthly, monthly, semi-monthly, weekly, semi-weekly, daily, hourly, a minute or a few minutes, or any combination of these intervals.

Preferably, the air oxidation haircolor composition is applied more frequently upon initial use of the product until the desired color is achieved, and then the frequency of use is reduced to simply maintain the desired color. For example, the air oxidation haircolor composition may be applied daily for the first 1-2 weeks, every other day for the third week, and then once a week thereafter. As another example, the air oxidation haircolor composition may be applied once a week or twice a week until the desired color is achieved and then it may be applied monthly or semi-monthly to maintain the desired color.

Removing the air oxidation haircolor composition may be conducted by any means known in the art, including, but not limited to, rinsing or wiping off. Preferably, rinsing is conducted using water. The removal, preferably, is the same as that for the type of grooming product the air oxidation haircolor composition is formulated to function. That is, for example, if the air oxidation haircolor composition is a shampoo, it is preferably rinsed off the hair with water.

Removing the air oxidation haircolor composition may be done directly after application. Removal directly after application as used herein refers to the removal regimen or procedure traditionally followed by consumers for the type of grooming product that the air oxidation haircolor composition is formulated to function. For example, if the air oxidation haircolor composition is a shampoo, the air oxidation haircolor composition may be removed in accordance with the consumer's usual procedure for removal of shampoo, and if the air oxidation haircolor composition is a conditioner, the air oxidation haircolor composition may be removed in accordance with the consumer's usual procedure for removal of conditioner. For example, directly after application may refer to a time period that is about 1 hour or less (i.e., within about 1 hour). With respect to cleansing and shampooing, removing may occur, for example, within about 15 minutes, within about 10 minutes, within about 9 minutes, within about 8 minutes, within about 7 minutes, within about 6 minutes, within about 5 minutes, within about 4 minutes, within about 3 minutes, within about 2 minutes, within about 1 minute after application, or within any time period in between. With respect to conditioning, removing may occur, for example, within about 1 hour, within about 45 minutes, within about 30 minutes, within about 15 minutes, within about 10 minutes, within about 9 minutes, within about 8 minutes, within about 7 minutes, within about 6 minutes, within about 5 minutes, within about 4 minutes, within about 3 minutes, within about 2 minutes, within about 1 minute after application, or within any time period in between. For example, removing directly after application may take place from about 10 minutes to about 15 minutes after application, or from about 3 minutes to about 5 minutes after application.

As noted above, the air oxidation haircolor composition may be in the form of an air oxidation haircolor conditioner composition or an air oxidation haircolor cleanser composition. An air oxidation haircolor conditioner composition simultaneously gradually colors and conditions the hair to which it is applied. An air oxidation haircolor cleanser composition may be, for example, a body wash, a face wash and/or a shampoo. An air oxidation haircolor cleanser composition as disclosed herein can simultaneously gradually color and cleanse the hair to which it is applied.

Hair refers to any hair on the body, including, but not limited to, head, face, and body hair. Preferably, the hair is head hair.

Any primary oxidation dye intermediate or a combination thereof suitable for an air oxidation hair dye may be used in the air oxidation haircolor composition disclosed herein. Oxidation dyes are primarily aromatic compounds and typically have a low molecular weight. Oxidation dyes form the basis of hair dyes and are generally categorized under two groups: oxidation base (primary intermediate) and coupler (secondary intermediate). Thus, the primary oxidation dye intermediate forms the base of a permanent hair coloring product.

In a certain embodiment, the primary oxidation dye intermediate is selected from the group consisting of: p-phenylenediamine, N,N-bis(2-hydroxyethyl)-p-phenylenediamine sulfate, p-aminophenol, 2,4,5,6-tetraaminopyrimidine, p-toluenediamine, 2-chloro-p-phenylenediamine, N-phenyl-p-phenylenediamine, p-methylaminophenol, 1-amino-4-(2-methoxyethyl)-aminobenzene, 2-(hydroxymethyl)-p-phenylenediamine, 3-methyl-p-aminophenol, 2-(2- hydroxyethyl)-p-phenylenediamine, 4,4'-diaminodiphenylamine, 1,3-dimethyl-2,5-diaminobenzene, 2-isopropyl-p-phenylenediamine, N-(beta-hydroxypropyl)-p-phenylenediamine, 2-methyl-p-aminophenol, N-2-methoxyethyl-p-phenylenediamine, 2-hydroxyethyl-p-phenylenediamine, 2,6-dimethyl-p-phenylenediamine, 3-methyl-p-aminopheol, 2-propyl-p-phenylenediamine, 2-(2'-hydroxyethylaminomethyl)-p-aminophenol, 2-(methoxymethyl)-p-aminophenol, 2-methyl-4-dimethylaminoaniline, 5-aminosalicylic acid, 2,3-dimethyl-p-phenylenediamine, 2,6-diethyl-p-phenylenediamine, 2,5-dimethyl-p-phenylenediamine, N,N-diethyl-p-phenylenediamine, N,N-dipropyl-p-phenylenediamine, 4-amino-N,N-diethyl-3-methylaniline, 4-N,N-bis(2-hydroxyethyl)-amino-2-methylanilin, 4-N,N-bis(2-hydroxyethyl)-amino-2-chloroaniline, 2-(2-hydroxyethyl)-p-phenylenediamine, 2-fluoro-p-phenylenediamine, N-(2-hydroxypropyl)-p-phenylenediamine, 2-hydroxymethyl-p-phenylenediamine, N,N-dimethyl-2-methyl-p-phenylenediamine, N-ethyl-N-(2-hydroxyethyl-p-phenylenediamine, N-(2,3-dihydroxypropyl)-p-phenylenediamine, N-(4' aminophenyl)-p-phenylenediamine, 2-(2-hydroxyethloxy)-p-phenylenediamine, 2-(acetylaminoethyloxy)-p-phenylenediamine, 2-methyl-1-N-(2-hydroxyethyl)-p-phenylenedamine, 4-methyl-o-phenylenediamine, a salt thereof, and any combination thereof.

In certain embodiments, depending on the desired shading and depth of color, the primary oxidation dye intermediate content is about 0.01% to about 5% weight by weight, preferably, about 0.1% to about 3.0% weight by weight, more preferably, about 1.0% to about 3.0% weight by weight, and most preferably, about 0.5% to about 2.0% weight by weight of the air oxidation haircolor composition. Preferably, the primary oxidation dye intermediate may be N,N-bis(2-hydroxyethyl)-p-phenylenediamine sulfate, or a salt thereof. In other certain embodiments, the air oxidation haircolor composition comprises about 0.01% to about 5% weight by weight, preferably, about 0.1% to about 3.0% weight by weight, more preferably, about 1.0% to about 3.0% weight by weight, and most preferably, about 0.5% to about 2.0% weight by weight of N,N-bis(2-hydroxyethyl)-p-phenylenediamine sulfate, or a salt thereof.

Any aromatic triol or a combination thereof that can function as a dye coupler in an air oxidation hair dye may be used. The aromatic triol controls the speed at which the dye intermediate oxidizes in the presence of atmospheric oxygen. The aromatic triol(s) and primary oxidation dye intermediate(s) in combination form the oxidation condensate, which, upon application, becomes trapped within the structure of the hair and rapidly oxidizes upon exposure to atmospheric oxygen.

In a certain embodiment, the aromatic triol is selected from the group consisting of: 1,2,4-benzenetriol, 2,4,5-trihydroxytoluene, pyrogallol, and any combination thereof. Depending upon the desired depth of color and speed of coloration, the aromatic triol content is about 0.01% to about 5% weight by weight, preferably, about 0.1% to about 3.0% weight by weight, and more preferably, about 0.2% to about 1.5% weight by weight of the air oxidation haircolor composition. In a preferred embodiment, the aromatic triol is 1,2,4-benzenetriol, and its content in the air oxidation haircolor composition is about 0.01% to about 5% weight by weight, preferably, about 0.1% to about 3.0% weight by weight, more preferably, about 0.2% to about 1.5% weight by weight, and most preferably, about 0.5% to about 0.9% weight by weight. In an embodiment, the aromatic triol, such as 1,2,4-benzenetriol, has a purity of greater than about 95%, preferably greater than about 97%, and more preferably greater than about 98%.

The air oxidation haircolor composition comprises water, which may be present in the amount of about 40% to about 98% weight by weight of the composition. The water content may also be about 70% to about 98% weight by weight, and more preferably, about 70% to about 85% weight by weight of the air oxidation haircolor composition. The water content of the composition (including the aqueous portion of surfactants) should be sufficient to allow for efficient transference of dye intermediates from solution to the interior of the hair shaft. As with other ingredients, the amount of water may be guided by what type of composition the hair dye is formulated to function. For example, high lather shampoos preferably have a lower water content than a light conditioner, which typically contain at least about 90% of water (including the aqueous portion of surfactants).

The air oxidation haircolor composition may also comprise at least one cleansing surfactant. Surfactants are added to reduce the surface tension of water and also the interfacial tension between oil and water. Thus, they have the ability to quickly wet out the hair surface. Surfactants can produce a lather and can allow for ease of rinsing. The surfactant content in the product varies by the type of grooming product, amount of water, and the other ingredients in the grooming product. Shampoos, cleansers, and body washes contain the highest surfactant levels. The cleansing surfactant content is preferably from greater than 5% to about 50% weight by weight, preferably about 7% to about 45% weight by weight, and more preferably about 10% to about 40% weight by weight of the air oxidation haircolor composition. For a shampoo, preferably, the surfactant content is about 6% to about 40% weight by weight, and more preferably, about 10% to about 20% weight by weight of the air oxidation haircolor composition. For a body wash or other cleanser, the surfactant content may be the same as that for a shampoo, but preferably, the surfactant content is greater than 5% to about 30% weight by weight, and more preferably, about 6% to about 15% weight by weight of the total air oxidation haircolor composition.

The surfactants used in the air oxidation haircolor composition disclosed herein can be any cosmetically acceptable surfactant. If the composition is intended, for example, to be a cleansing composition, the surfactant may be any anionic, amphoteric or nonionic cleansing surfactant, or any combination thereof. In a certain embodiment, the cleansing surfactant is selected from the group consisting of: alkyl sulfate, alkyl ether sulfate, fatty acid soap, alkyl glyceryl ether sulfonate, methyl alkyl taurate, fatty alkyl glycinate, N-alkyl glutamate, alkylisethionate, alkyl ethoxysulfosuccinate, alpha-sulfonated fatty acid, alkyl ethoxy carboxylate, alkyl phosphate ester, amphoacetate, alkyl polyglycoside, amphodiacetate, amphohydroxypropylsulfonate, amphopropionate, amidopropyl betaine, sultaine, alkylamidopropylamine oxide, alkylamine oxide, alkanolamide, sulfocuccinate, alkylamphopropionate, ethoxylated fatty alcohol, fatty ester and ethoxylate thereof, propoxylated fatty alcohol, glycerolated fatty alcohol, fatty diol, fatty alkylphenol, fatty amide, methylacyl taurate, fatty acyl glycinate, N-acyl glutamate, alkyl ethoxysulphosuccinate, alkyl phosphate ester, ethoxylated alkyl phosphate ester, acylsarcosinate, triglyceride with an inserted polyethyleneglycol chain, ethoxylated mono and di-glyceride, polyethoxylated lanolin, ethoxylated butter derivative, alkyl betaine, and any combination thereof.

Surfactant molecules in water have the ability to self-assemble at concentrations greater than a critical micelle concentration (CMC) into several types of supra molecular aggregates called micelles. The lowest concentration at which micelles are formed is the CMC. A micelle typically forms with the hydrophilic "head" regions in contact with surrounding water sequestering the hydrophobic single-tail regions in the micelle center. Surfactant aggregates include spheres (micellar phase), cylinders (hexagonal phase), or bilayers (lamellar phase) depending on the amount and type of surfactant that is employed. Formulations having spherical micelles tend to have low viscosity and Newtonian flow properties and may not have properties that are desirable for a shampoo. Cylindrical micelles are generally larger in size than spherical micelles. Formulations with cylindrical micelles are more viscous because movement of these larger micelles is restricted.

Most conventional shampoos are cylindrical phase emulsions as the production of these formulations is cost-effective and the viscosity can be achieved by adding salts that increase the size of the micelles. However, both spherical and cylindrical micellar formulations do not have the ability to hold oils, actives and other particulate materials. In addition, due to the small size of spherical micelles, the micelles may penetrate into the skin stratum corneum or eye membrane and thus cause undesirable irritation and harshness of any grooming product containing these formulations.

Surfactant mixtures in water can also form stacks of ordered bilayers called a lamellar phase. Within the lamellar phase, the surfactant molecules are arranged into bilayers that are separated by water layers. Lamellar phase compositions have high zero shear viscosity due to the close packed layered arrangement. The layers are flat and each parallel layer can slide over adjacent layers, which results in the shear thinning behavior of lamellar phase compositions.

Preferably, at least about 80 weight %, more preferably at least about 85 weight %, still more preferably at least about 90 weight %, still more preferably at least about 95 weight %, still more preferably at least about 98 weight %, still more preferably at least about 99 weight %, still more preferably about 100 weight % or all of the surfactants that are in the air oxidation haircolor composition can form bilayers. Without wishing to be bound by a theory, it is believed that, in the lamellar phase, the hair dye molecules are trapped between the layers creating an encapsulated effect, which protects the dyes from exposure to air and imparts superior properties to the grooming product. Such properties include a creamy texture, decreased staining and increased stability during storage (i.e., reduced premature oxidation). Thus, cleansing surfactants that form these bilayers may be employed in air oxidation haircolor compositions to reduce or prevent staining by the dye of skin or other surfaces, and provide enhanced protection against premature oxidation of the colorant. In a shampoo composition, such surfactants improve the stability of the dye(s), create a superior texture and also make the composition appear more like a premium conventional shampoo in terms of color, appearance, moisturization and conditioning.

In an embodiment of the air oxidation haircolor composition disclosed herein, the cleansing surfactant forms a lamellar phase. Preferably, the cleansing surfactant, which forms a lamellar phase, is selected from the group consisting of: at least one anionic cleansing surfactant selected from the group of sulfosuccinates and isethionates, at least one amphoteric cleansing surfactant selected from the group of sultaines and betaines, and at least one nonionic cleansing surfactant selected from the group of alkyl poly glucosides, and any combination thereof. Preferably, this cleansing surfactant also comprises at least one fatty derivative or mixture thereof. Preferably, the fatty derivative may be a mixture of a fatty alcohol (e.g., cetearyl alcohol, cetyl alcohol, stearyl alcohol, lauryl alcohol, capric alcohol) and fatty acid ester, or a mixture of a fatty acid and a fatty amide. Preferably, the sulfosuccinate may be selected from the group consisting of dioctyl sodium sulfosuccinate, disodium lauryl sulfosuccinate, disodium laureth sulfosuccinate, disodium oleamide MEA sulfosuccinate, sodium dialkyl sulfosuccinate, and any combination thereof. Preferably, the betaine may be selected from the group consisting of cocamidopropyl betaine, lauramidopropyl betaine, coco betaine, lauryl betaine, cetyl betaine, babussuamidopropyl betaine, wheatgermamidopropyl betaine, oleamidopropyl betaine, capryl/capramidopropyl betaine, tallow dihydroxyethyl betaine, and coco alkyldimethyl betaine, as well as any combination thereof, and the sultaine may be selected from the group consisting of cocamidopropyl hydroxysultaine, lauramidopropyl hydroxysultaine, lauryl hydroxysultaine, capryl hydroxysultaine, cetyl hydroxysultaine, caprylamidopropyl hydroxysultaine, and oleamidopropyl hydroxysultaine, as well as any combination thereof. Preferably, the alkyl poly glucoside may be selected from the group consisting of decyl glucoside, cetyl glucoside, cetearyl glucoside, lauryl glucoside, coco glucoside, and any combination thereof. Preferably, the isethionate may be selected from the group consisting of sodium cocoyl isethionate, ammonium cocoyl isethionate, sodium lauroyl isethionate, sodium lauroyl methyl isethionate, and any combination thereof.

In an embodiment, the cleansing surfactant is a combination of at least one anionic cleansing surfactant selected from the group of at least one sulfosuccinate and at least one isethionate, at least one sultaine, at least one alkyl poly glucoside, and at least one fatty derivative. In another embodiment, the cleansing surfactant is a combination of at least one sulfosuccinate, at least one sultaine, at least one alkyl poly glucoside, at least one isethionate, and at least one fatty derivative, and the content of this combination in the air oxidation haircolor composition is about 3% to about 50%, greater than about 5% to about 45%, preferably greater than about 5% to about 10% weight by weight. In an embodiment, the air oxidation haircolor composition comprises about 3% to about 7% weight by weight, preferably about 4.5% to about 5.5% weight by weight, of at least one sulfosuccinate, about 0.5% to about 5% weight by weight, preferably about 1% to about 3% weight by weight, of at least one sultaine, about 1% to about 5% weight by weight, preferably about 2% to about 3% weight by weight, of at least one glucoside, and about 0.5% to about 4% weight by weight, preferably about 1.5% to about 2.5% weight by weight, of at least one isethionate. The fatty derivative may be present in about 1% to about 5% weight by weight, preferably about 2% to about 4% weight by weight, of the air oxidation haircolor composition. In a certain embodiment, the fatty derivative is a fatty alcohol, and preferably may be cetearyl alcohol.

The air oxidation haircolor composition may also comprise at least one conditioning agent. The conditioning agents may be present in a shampoo, cleanser or conditioner type air oxidation haircolor composition. Any conditioning agent may be used. In a certain embodiment, the conditioning agent is selected from the group consisting of: quaternized gum, quaternized polymer, quaternary ammonium salt, synthetic oil, plant oil, natural or synthetic wax, silicone, fatty amine, cationic and aminofunctional polysiloxane, quaternized protein, quaternized polysaccharide, polyamine, polyaminoamide, cationic cellulose, quaternary polymer of vinyl pyrrolidone and vinylimidazole, polyalkylenimine, and any combination thereof. The conditioning agent content may be about 0.1% to about 15% weight by weight, preferably, about 2% to about 10% weight by weight of the air oxidation haircolor composition.

The air oxidation haircolor composition may also comprise a grooming agent selected from the group consisting of: at least one cleansing surfactant; at least one conditioning agent; and any combination thereof. In an embodiment thereof, a cleansing surfactant content is greater than 5% to about 50% weight by weight, and a conditioning agent content is about 0.5% to about 15% weight by weight, or about 0.1% to about 15% weight by weight.

The air oxidation haircolor composition may also comprise at least one auxiliary oxidation dye coupler. The auxiliary oxidation dye coupler is used for developing the shade and achieving a broader spectrum of color imparted by the air oxidation haircolor composition. The auxiliary oxidation dye coupler may be selected from the group consisting of: resorcinol, 4-chlororesorcinol, 2-methylresorcinol, m-aminophenol, 1-naphthol, 1,5-naphthalenediol, 2,7-napthalenediol, 2,4-diaminophenol, hydroxybenzomorpholine, 1-hydroxy-3-dimethylaminobenzene, 4-amino-2-hydroxytoluene, 2-methyl-5-hydroxyethylaminophenol, 1-methoxy-2,5-diaminobenzene, phenyl methyl pyrazolone, 2,4-diaminophenoxyethanol HCl, 4-ethoxy-m-phenylenediamine, 1-hydroxy-3-amino-4,6-dichlorobenzene, 1-hydroxy-2,5-diamino-4-methoxybenzene, 4-amino-m-cresol, 6-amino-m-cresol, 2-amino-4-hydroxyethylaminoanisole, 5-amino-6-chloro-o cresol, 6-amino-o-cresol, 4,6-bis(2-hydroxyethoxy)-m-phenylenediamine HCl, 5-amino-4-chloro-o-cresol, 2-ethylamino-p-cresol, 2-amino-5-acetaminophenol, 2-methyl-1-naphthol, 1-acetoxy-2-methylnaphthalene, 1-hydroxy-6-aminonaphthalene-3-sulfonic acid, thymol, 1,5-dihydroxy-1,2,3,4-tetrahydronaphthalene, 2-chlororesorcinol, N,N-bis(hydroxyethyl)-m-phenylenediamine, 2,6-diaminotoluene, N,N-bis(hydroxyethyl)-2,4-diaminophenetole, 4,6-bis(hydroxyethyl)-m-phenylenediamine, 6-hydroxybenzomorpholine, 2-hydroxy-4-hydroxyethyl-aminotoluene, 4,6-dichloro-m-aminophenol, 2-methyl-m-aminophenol, 2-chloro-6-methyl-m-aminophenol, 2-hydroxyethoxy-5-aminophenol, 2-chloro-5-trifluoroethylaminophenol, 4-chloro-6-methyl-m-aminophenol, N-hydroxyethyl-4-methoxy-2-methyl-m-aminophenol, 5-amino-4-methoxy-2-methylphenol, 2-dimethylamino-5-aminopyridine, 6-methoxy-8-aminoquinoline, 2,6-dihydroxy-4-methylpyridine, 2,6-dihydroxy-3,4-dimethylpyridine, 5-chloro-2,3-dihydroxypyridine, 4-hydroxyindole, 5,6-dihydroxyindole, 7-hydroxyindole, 5-hydroxyindole, 2,3-dihydroxynaphthalene, 5-methyl-o-aminophenol, 6-methyl-o-aminophenol, 2-amino-5-acetaminophenol, 1,7-dihydroxynaphthalene, 1-hydroxy-6-aminonaphthalene-3-sulfonic acid, 2,3-dihydroxy-1,4-naphthoquinone, 3,4-methylenedioxy-1((beta-hydroxyethyl)amino)benzene, 3,4-methylenedioxyphenol, 1-methoxy-2-amino-4-((beta-hydroxyethyl)amino)benzene, 1-naphthol-4-sulfonic acid, m-phenylenediamine, 2,6-diaminotoluene, N,N-bis(hydroxyethyl)-2,4-diaminophenetole, bis(2,4-diaminophenoxy)-1,3-propane, 1-hydroxyethyl-2,4-diaminobenzene, aminoethoxy-2,4-diaminobenzene, 2,4-diaminophenoxyacetic acid, 2,4-diamino-5-methylphenetole, 2,4-diamino-5-hydroxyethoxytoluene, 2,4-dimethoxy-1,3-diaminobenzene, 2,6-bis(hydroxyethylamino)-toluene, 2-hydroxy-4-carbamoylmethylaminotoluene, 2-Chloro-6-methyl-m-aminophenol, 2-hydroxyethoxy-5-aminophenol, N-cyclopentyl-3-aminophenol, N-hydroxyethyl-4-methoxy-2-methyl-m-aminophenol, 5-amino-4-methoxy-2-methylphenol, 6-methoxy-8-aminoquinoline, 5-hydroxy-1,4-benzodioxane, 3,4-methylenedioxyphenol, 4-hydroxyethylamino-1,2-methylenedioxybenzene, 2,6-dihydroxy-3,4-dimethylpyridine, and any combination thereof. Depending upon the desired resulting depth of shade, the auxiliary oxidation dye coupler content may be about 0.001% to about 5% weight by weight, preferably, about 0.001% to about 3% weight by weight of the air oxidation haircolor composition.

The air oxidation haircolor composition may also comprise at least one antioxidant. The antioxidant content in the composition may be adjusted to delay the onset of color in order to minimize potential staining of the skin, or simply added in small amounts to increase the absorption of the dye on the hair. When used, the antioxidant content may be about 0.02% to about 1% weight by weight of the air oxidation haircolor composition. Increasing the antioxidant content further may result in poor color deposition in the hair. Any antioxidant or reducing agent, or a combination thereof, may be used, including, but not limited to, sodium sulfite, bisulfite salt, thioglycolate salt, erythorbic acid, ascorbic acid, thiosulfate salt, ascobylated compounds, cysteine, sodium hydrosulfite, thiourea, thiolactic acid, glyceryl monothioglycolate, thioglycerol, 2,5-dihydroxybenzoic acid, zinc formosulfoxylate, and any combination thereof.

The air oxidation haircolor composition may also comprise at least one catalyst. A catalyst may be added to speed up the oxidation process. The catalyst content may be about 0.01% to about 1.0% weight by weight, preferably, about 0.05% to about 0.5% weight by weight, and more preferably about 0.1% to about 0.4% weight by weight of the air oxidation haircolor composition. In a certain embodiment, the catalyst is a water soluble transition metal such as copper, cobalt, zinc, silver, nickel and/or iron. In another embodiment, the catalyst is a metal, a metal salt and/or a metal complex, wherein the metal is selected from the group consisting of: manganese, copper, cobalt, zinc, silver, nickel, chromium, vanadium, molybdenum, osmium, ruthenium, rhodium, palladium, platinum, cadmium, iron, and any combination thereof. The salt may be selected from the group consisting of: sulfate, chloride, nitrate, carbonate, phosphate, fumarate, citrate and/or tartrate. Preferably, the catalyst is a manganese salt.

The pH of the air oxidation haircolor composition is preferably from about 4 to about 9, and, more preferably, from about 5 to about 8. Thereby, the composition is milder and less irritating than dyes presently on the market. Because of the more neutral pH, the composition disclosed herein may be used frequently, and even daily, by consumers with minimal to no irritation and dryness of the skin or scalp.

At least one acid or alkalizer may be added to the air oxidation haircolor composition to achieve the desired pH. Any acid or alkalizer suitable for application to hair may be used. The acid or alkalizer content may be about 0.01% to about 5.0% weight by weight, preferably from about 0.1% to about 2.0% weight by weight of the air oxidation haircolor composition. The acid or alkalizer may be organic or inorganic. In a certain embodiment, the air oxidation dye composition comprises an alkalizer selected from the group consisting of: ethanolamine, triethanolamine, aminomethyl propanol, ammonium hydroxide, carbonates, bicarbonate, isopropanolamine, propane-1,3-diamine, oxyethylenated and oxypropylenated hydroxyalkylamine and ethylenediamine, polyamine, sodium and potassium hydroxide, alkali silicate, alkali metasilicate, and any combination thereof. In another embodiment, the air oxidation dye composition comprises an acid selected from the group consisting of: hydrochloric acid, tartaric acid, citric acid, ascorbic, acid, acetic acid, lactic acid, sulfuric acid, formic acid, phosphoric acid, etidronic acid, boric acid, nitric acid, phosphorous acid, oxalic acid, and any combination thereof.

To achieve adequate viscosity and desirable rheological properties to allow for ease of application of the composition and adherence to the hair, at least one thickener may be added to the air oxidation haircolor composition. The type of thickener that may be used is not particularly limited but should be suitable for application to hair. The thickener may be selected from the group consisting of: a nonionic, anionic, cationic, or amphoteric polymer, a saturated or unsaturated long chain fatty acid, carboxmethylcellulose, sodium alginate, a crosslinked homopolymer of acrylic acid or of acrylamidopropanesulfonic acid or associative polymer, hydroxyethyl cellulose, hydroxypropyl cellulose, guar gum, xanthan gum, scleroglucan gum, and quaternized version of hydroxyethyl cellulose, hydroxypropyl cellulose, guar gum, scleroglucan gum; a saturated or unsaturated long chain fatty alcohol having from about 11 to about 18 carbon atoms alone or in combination with an ethoxylate or a propoxylate of a long chain fatty alcohol; and any combination thereof. The thickener content may be about 0.1% to about 8% weight by weight, preferably from about 1.5% to about 6% weight by weight of the air oxidation haircolor composition.

The air oxidation haircolor composition may also comprise at least one chelating agent. A chelating agent may be added to increase the stability of the product by decreasing the presence of metal ions, which otherwise, if present, might cause damage to or undesirably color the hair. The chelating agent may be selected from the group consisting of: EDTA, a sodium salt of EDTA, HEDTA, etidronic acid, citric acid, aminopolycarboxylic acid, 2,3-dihydroxybenzoic acid, dimercaptosuccinic acid, iminodiacetic acid, gluconic acid, trisodium citrate, and any combination thereof. The chelating agent content may be about 0.01% to about 5.0% weight by weight, preferably from about 0.1% to about 0.5% weight by weight of the air oxidation haircolor composition.

The air oxidation haircolor composition may also comprise at least one anti-dandruff agent. Any anti-dandruff agent may be used, including, but not limited to, pyrithione zinc, coal tar, salicylic acid, selenium sulfide and/or sulfur. The anti-dandruff agent content may be 0.1% to about 5.0% weight by weight, preferably from about 1.0% to about 2.0% weight by weight of the air oxidation haircolor composition.

The air oxidation haircolor composition may also comprise at least one hair regrowth active ingredient. The hair regrowth active ingredient may include, but is not limited to, minoxodil, and may be added in conventionally used amounts. For instance, the hair regrowth active ingredient content may be about 1% to about 10% weight by weight, preferably, from about 2% to about 5% weight by weight of the air oxidation haircolor composition.

Any other ingredients known for use in the art in the formulation of shampoos, cleansers and conditioners may also be added to the air oxidation haircolor composition, including but not limited to at least one opacifier, such as glycol stearate, stearamide AMP, at least one preservative, such as a paraben type preservative, and/or at least one fragrance.

The air oxidation haircolor composition may be applied to the hair from various types of containers. The container may be an aerosol or a non-aerosol container. An aerosol container creates an anaerobic environment, which may help to preserve the efficacy of the composition.

The air oxidation haircolor composition may be in the form of a liquid, solution, lotion, gel, cream, suspension or foam. Preferably, the air oxidation haircolor composition may be a gel, a cream that may be dispensed from a collapsible tube or canister, or a slightly viscous lotion suitable for dispensing from an aerosol container.

In an embodiment, a method for gradually coloring hair comprises the steps of: a) applying an air oxidation haircolor composition to hair; and b) removing the air oxidation haircolor composition from the hair directly after application, wherein the air oxidation haircolor composition comprises: 1) at least one primary oxidation dye intermediate, where a primary oxidation dye intermediate content is about 0.01% to about 5% weight by weight, and preferably, about 0.1% to about 3.0% weight by weight; 2) at least one aromatic triol, where an aromatic triol content is about 0.01% to about 5% weight by weight, and preferably, about 0.1% to about 3.0% weight by weight; and 3) water. In an embodiment thereof, the primary oxidation dye intermediate is N,N-bis(2-hydroxyethyl)-p-phenylenediamine sulfate, or a salt thereof and/or the aromatic triol is 1,2,4-benzenetriol. The application and removal of the air oxidation haircolor composition may be conducted in multiple spaced intervals.

In another embodiment, a method for gradually coloring hair comprises the steps of: a) applying an air oxidation haircolor composition to hair; and b) removing the air oxidation haircolor composition from the hair directly after application, wherein the air oxidation haircolor composition comprises: 1) at least one primary oxidation dye intermediate, where a primary oxidation dye intermediate content is about 0.1% to about 3.0% weight by weight; 2) at least one aromatic triol, where an aromatic triol content is about 0.1% to about 3.0% weight by weight; 3) water, where a water content is about 40% to about 98% weight by weight; and 4) at least one cleansing surfactant, where a cleansing surfactant content is greater than 5% to about 50% weight by weight and/or at least one conditioning agent, where a conditioning agent content is about 0.5% to about 15% weight by weight. The application and removal of the air oxidation haircolor composition may be conducted in multiple spaced intervals.

Another embodiment is a method for simultaneously cleansing and gradually coloring hair comprising the steps of: a) applying an air oxidation haircolor composition to hair; and b) removing the air oxidation haircolor composition from the hair directly after application, wherein the air oxidation haircolor composition is an air oxidation haircolor grooming composition comprising: 1) at least one primary oxidation dye intermediate, where a primary oxidation dye intermediate content is about 0.01% to about 5% weight by weight; 2) at least one aromatic triol, where an aromatic triol content is about 0.01% to about 5% weight by weight; 3) water, where a water content is about 40% to about 98% weight by weight; and 4) at least one cleansing surfactant, where a cleansing surfactant content is greater than 5% to about 50% weight by weight. The air oxidation haircolor grooming composition may be an air oxidation haircolor shampoo composition or an air oxidation haircolor and cleansing composition. The application and removal of the air oxidation haircolor composition may be conducted in multiple spaced intervals.

In the method for simultaneously cleansing and gradually coloring hair, the air oxidation haircolor composition may further comprise at least one anti-dandruff agent, at least one conditioning agent, at least one catalyst, at least one alkalizer, at least one acid, at least one thickener, at least one antioxidant, at least one chelating agent, at least one hair regrowth active agent or at least one auxiliary oxidation dye coupler.

The terms used in connection with this embodiment have the same meaning as the terms have with respect to the embodiments mentioned above.

Yet another embodiment is a method for simultaneously conditioning and gradually coloring hair comprising the steps of: a) applying an air oxidation haircolor composition to hair; and b) removing the air oxidation haircolor composition from the hair directly after application, wherein the air oxidation haircolor composition is an air oxidation haircolor grooming composition comprising: 1) at least one primary oxidation dye intermediate, where a primary oxidation dye intermediate content is about 0.01% to about 5% weight by weight; 2) at least one aromatic triol, where an aromatic triol content is about 0.01% to about 5% weight by weight; 3) water, where a water content is about 40% to about 98% weight by weight; and 4) at least one conditioning agent, where a conditioning agent content is about 0.1% to about 15% weight by weight. This method may further comprise the step of heating the hair after applying the air oxidation haircolor composition. The air oxidation haircolor grooming composition may be an air oxidation haircolor conditioner composition or an air oxidation haircolor and conditioning composition. The application and removal of the air oxidation haircolor composition may be conducted in multiple spaced intervals.

In the method for simultaneously conditioning and gradually coloring hair, the air oxidation haircolor composition may further comprise at least one catalyst, at least one alkalizer, at least one acid, at least one thickener, at least one antioxidant, at least one chelating agent, at least one hair regrowth active agent or at least one auxiliary oxidation dye coupler.

The terms used in connection with this embodiment have the same meaning as the terms have with respect to the embodiments mentioned above.

Yet another embodiment is a method for cleansing, conditioning and gradually coloring hair comprising the steps of: a) applying an air oxidation haircolor shampoo composition to hair in multiple spaced intervals; b) removing the air oxidation haircolor shampoo composition from the hair directly after application; c) applying an air oxidation haircolor conditioner composition to the hair; and d) removing the air oxidation haircolor conditioner composition from the hair directly after application, wherein the air oxidation haircolor shampoo composition comprises: 1) at least one primary oxidation dye intermediate, where a primary oxidation dye intermediate content is about 0.01% to about 5% weight by weight; 2) at least one aromatic triol, where an aromatic triol content is about 0.01% to about 5% weight by weight; 3) water, where a water content is about 40% to about 98% weight by weight; and 4) at least one cleansing surfactant, where a cleansing surfactant content is greater than 5% to about 50% weight by weight, and wherein the air oxidation haircolor conditioner composition comprises: 1) at least one primary oxidation dye intermediate, where a primary oxidation dye intermediate content is about 0.01% to about 5% weight by weight; 2) at least one aromatic triol, where an aromatic triol content is about 0.01% to about 5% weight by weight; 3) water, where a water content is about 40% to about 98% weight by weight; and 4) at least one conditioning agent, where a conditioning agent content is about 0.1% to about 15% weight by weight. Each or both of the air oxidation haircolor shampoo and conditioner compositions can be applied in multiple spaced intervals.

The air oxidation haircolor shampoo composition of this embodiment may further comprise at least one anti-dandruff agent, at least one conditioning agent, at least one catalyst, at least one alkalizer, at least one acid, at least one thickener, at least one antioxidant, at least one chelating agent, at least one hair regrowth active agent or at least one auxiliary oxidation dye coupler. The air oxidation haircolor conditioner composition of this embodiment may further comprise at least one catalyst, at least one alkalizer, at least one acid, at least one thickener, at least one antioxidant, at least one chelating agent, at least one hair regrowth active agent or at least one auxiliary oxidation dye coupler.

The terms used in connection with this embodiment have the same meaning as the terms have with respect to the embodiments mentioned above.

Yet another embodiment is an air oxidation haircolor shampoo composition comprising: 1) at least one primary oxidation dye intermediate, where a primary oxidation dye intermediate content is about 0.1% to about 3% weight by weight; 2) at least one aromatic triol, where an aromatic triol content is about 0.1% to about 3% weight by weight; 3) water, where a water content is about 40% to about 98% weight by weight; and 4) at least one cleansing surfactant, where a cleansing surfactant content is greater than 5% to about 50% weight by weight; wherein the air oxidation haircolor shampoo composition cleanses hair; and wherein the air oxidation haircolor shampoo composition simultaneously gradually colors hair with repeated use.

The air oxidation haircolor shampoo composition of this embodiment may further comprise at least one anti-dandruff agent, at least one conditioning agent, at least one catalyst, at least one alkalizer, at least one acid, at least one thickener, at least one antioxidant, at least one chelating agent, at least one hair regrowth active agent or at least one auxiliary oxidation dye coupler.

The terms used in connection with this embodiment have the same meaning as the terms have with respect to the prior embodiments.

Yet another embodiment is an air oxidation haircolor conditioner composition comprising: 1) at least one primary oxidation dye intermediate, where a primary oxidation dye intermediate content is about 0.1% to about 3% weight by weight; 2) at least one aromatic triol, where an aromatic triol content is about 0.1% to about 3% weight by weight; 3) water, where a water content is about 40% to about 98% weight by weight; and 4) at least one conditioning agent, where a conditioning agent content is about 0.1% to about 15% weight by weight; wherein the air oxidation haircolor conditioner composition conditions the hair; and wherein the air oxidation haircolor conditioner composition simultaneously gradually colors hair with repeated use.

The air oxidation haircolor conditioner composition of this embodiment may further comprise at least one catalyst, at least one alkalizer, at least one acid, at least one thickener, at least one antioxidant, at least one chelating agent, at least one hair regrowth active agent or at least one auxiliary oxidation dye coupler.

The terms used in connection with this embodiment have the same meaning as the terms have with respect to the embodiments mentioned above.

EXAMPLES

Specific embodiments of the disclosure will now be demonstrated by reference to the following general examples. It should be understood that these examples are disclosed solely by way of illustration and should not be taken in any way to limit the scope of the present disclosure.

Example 1: Air Oxidation Haircolor Conditioner Composition

An air oxidation haircolor conditioner composition was prepared using the ingredients set forth in Table 1 below.

TABLE 1

| TRADE NAME and function | INCI NAME | % WT/WT | % ACTIVE |
|---|---|---|---|
| Water, Deionized (solvent) | Water | 77.989% | 90.400% |
| FCC Kosher Erythorbic Acid (antioxidant) | Erythorbic Acid | 0.200% | 0.200% |
| Anhydrous Food Grade Sodium Sulfite (antioxidant) | Sodium Sulfite | 0.300% | 0.300% |
| Dequest 2010 (chelating agent) | Etidronic Acid | 0.100% | 0.100% |
| Emulgade 1000 Ni (thickener) | Cetearyl Alcohol (80%) & Ceteareth-20 (20%) | 5.000% | 4.000% 1.000% |
| Glycerox HE (emulsifier) | PEG-7 Glyceryl Cocoate | 3.000% | 3.000% |
| Incroquat Behenyl TMS (conditioner) | Behentrimonium Methosulfate (25%) & Cetearyl Alcohol (75%) | 2.700% | 0.675% 2.025% |
| Dow Corning 200 fluid (conditioner) | Dimethicone | 4.000% | 4.000% |
| Brij 721 (emulsifier) | Steareth-21 | 0.500% | 0.500% |
| Belle Aire "Cool Water" Type OM# 88813 (olfactory enhancement) | Fragrance | 0.500% | 0.500% |
| Monoethanolamine Technical Grade (alkalizer) | Ethanolamine | 1.210% | 0.290% free amine remaining |
| Rodol P Base (primary dye intermediate) | p-Aminophenol | 0.100% | 0.100% |
| Manganese Sulfate Monohydrate (catalyst) | Manganese Sulfate | 0.200% | 0.200% |
| Neolone PE (preservative) | Methylisothiazolinone (2.0%) & Phenoxyethanol (85%) & Propanediol (13%) | 0.500% | 0.010% 0.425% 0.065% |
| Rodol Gray HED (primary dye intermediate) | N,N-Bis(2-Hydroxyethyl)-p-Phenylenediamine Sulfate | 0.700% | 0.700% |
| Benzenetriol Premix (dye coupler) | 1,2,4-Trihydroxybenzene (20%) Acetic Acid (28.57%) Sulfuric Acid (1.3%) Water (50.13) | 3.000% | 0.600% 1.728*% 0.088**% 1.504% |
| Lipo Melanin C (pigment) | Melanin (10%) Pentylene Glycol (90%) | 0.001% | 0.0001% 0.0009% |
| | TOTAL | 100.000% | 100.000% |

*as Acetamide MEA
**as Aminoethyl Sulfate

Example 2: Air Oxidation Haircolor Shampoo Composition

An air oxidation haircolor shampoo composition was prepared using the ingredients set forth in Table 2 below.

TABLE 2

| TRADE NAME and function | INCI NAME | % WT/WT | % ACTIVE |
|---|---|---|---|
| Water, Deionized (solvent) | Water | 49.269% | 83.520% |
| FCC Kosher Erythorbic Acid (antioxidant) | Erythorbic Acid | 0.200% | 0.200% |
| Anhydrous Food Grade Sodium Sulfite (antioxidant) | Sodium Sulfite | 0.300% | 0.300% |
| Dequest 2010 (chelating agent) | Etidronic Acid | 0.030% | 0.030% |
| Steol CA-230-D (surfactant) | Ammonium Laureth Sulfate (25%) | 20.000% | 5.000% |
| Mackamine CAO (surfactant) | Cocamidopropylamine Oxide (30%) | 3.000% | 1.000% |

TABLE 2-continued

| INGREDIENTS | | | |
|---|---|---|---|
| TRADE NAME and function | INCI NAME | % WT/WT | % ACTIVE |
| Jaguar C13S (thickener &conditioner) | Guar Hydroxypropyltrimonium Chloride | 1.000% | 1.000% |
| Rhodacal A-246/L (surfactant) | Sodium Alpha Olefin Sulfonate (39%) | 15.000% | 5.850% |
| Montanov 68 (thickener) | Cetearyl Alcohol (80%) & Cetearyl Glucoside (20%) | 1.500% | 1.200% 0.300% |
| Belle Aire "Cool Water" Type OM# 88813 (olfactory enhancement) | Fragrance | 1.000% | 1.000% |
| Monoethanolamine Technical Grade (alkalizer) | Ethanolamine | 1.600% | 0.058% Free amine remaining |
| DL Panthenol (humectant & conditioner) | Panthenol | 0.100% | 0.100% |
| Manganese Sulfate Monohydrate (catalyst) | Manganese Sulfate | 0.200% | 0.200% |
| Neolone PE (preservative) | Methylisothiazolinone (2.0%) & Phenoxyethanol (85%) & Propanediol (13%) | 0.500% | 0.010% 0.425% 0.065% |
| Rodol Gray HED (primary dye intermediate) | N,N-Bis(2-Hydroxyethyl)-p-Phenylenediamine Sulfate | 1.800% | 1.800% |
| Benzenetriol Premix (dye coupler) | 1,2,4-Trihydroxybenzene (20%) Acetic Acid (28.57%) Sulfuric Acid (1.3%) Water (50.13) | 4.500% | 0.900% 2.786*% 0.142**% 2.255% |
| Lipo Melanin C (pigment) | Melanin (10%) Pentylene Glycol (90%) | 0.001% | 0.0001% 0.0009% |
| TOTAL | | 100.000% | 100.000% |

*as Acetamide MEA
**as Aminoethyl Sulfate

To make the air oxidation haircolor shampoo composition, the deionized water was poured into a stainless steel kettle with a sweep action mixer. The Jaguar C13S was then added while mixing and mixing continued for 30-60 minutes. A kettle was then heated to 70-78° C. While heating, Steol CA-230-D, Mackamine CAO, Rhodacal A-246/L, Mackamine CAO, and Montanov 68 were each added separately while mixing. The solution was mixed until all solids were completely dissolved. Dequest 2010, Erythorbic Acid, Sodium Sulfite, Manganese Sulfate, and Panthenol were then each added to the solution separately while mixing with each ingredient dissolved completely before adding the next. Rodol Gray HED was then added and the solution was mixed until dissolution was complete and the solution was mixed for an additional 20-30 minutes. The mix was then cooled to 50-55° C. Then benzenetriol was added while mixing. The mix was then cooled to 40-45° C. Then Neolone PE, fragrance, monoethanolamine and melanin were each added separately while mixing to a uniform solution before adding the next. The mix was then transferred to the holding tank under anaerobic conditions.

Example 3: Air Oxidation Haircolor Shampoo Composition (Low-Stain)

A low-stain air oxidation haircolor shampoo composition was prepared using the ingredients set forth in Table 3 below. Specifically, the addition of cocamidopropyl hydroxysultaine, disodium lauryl sulfosuccinate, sodium cocoyl isethionate, decyl glucoside, and the mixture of cetearyl alcohol, and cetearyl glucoside creates a lamellar phase composition in which the dyes are protected from air oxidation and hence contributes to the low-stain properties of this air oxidation haircolor shampoo composition.

TABLE 3

| INGREDIENTS | | | |
|---|---|---|---|
| TRADE NAME and function | INCI NAME | % WT/WT | % ACTIVE |
| Water, Deionized (solvent) | Water | 65.219% | 85.820% |
| FCC Kosher Erythorbic Acid (antioxidant) | Erythorbic Acid | 0.200% | 0.200% |
| Anhydrous Food Grade Sodium Sulfite (antioxidant) | Sodium Sulfite | 0.300% | 0.300% |
| Dequest 2010 (chelating agent) | Etidronic Acid | 0.030% | 0.030% |
| Mackam CBS 50G (surfactant) | Cocamidopropyl Hydroxysultaine (40%) | 4.000% | 1.600% |
| Mackanate LO (surfactant) | Disodium Lauryl Sulfosuccinate (40%) | 10.000% | 4.000% |

TABLE 3-continued

| TRADE NAME and function | INCI NAME | % WT/WT | % ACTIVE |
|---|---|---|---|
| Jaguar C13S (thickener & conditioner) | Guar Hydroxypropyltrimonium Chloride | 1.000% | 1.000% |
| Hostapon SCI 85C (surfactant) | Sodium Cocoyl Isethionate (85%) | 2.000% | 1.700% |
| Plantaren 2000 (surfactant) | Decyl Glucoside (50%) | 5.000% | 2.500% |
| Montanov 68 (thickener) | Cetearyl Alcohol (80%) & Cetearyl Glucoside (20%) | 2.500% | 2.000% 0.500% |
| Belle Aire "Cool Water" Type OM# 88813 (olfactory enhancement) | Fragrance | 0.750% | 0.750% |
| Monoethanolamine Technical Grade (alkalizer) | Ethanolamine | 1.900% | 0.358% Free amine remaining |
| DL Panthenol (humectant & conditioner) | Panthenol | 0.100% | 0.100% |
| Manganese Sulfate Monohydrate (catalyst) | Manganese Sulfate | 0.200% | 0.200% |
| Optiphen Plus (preservative) | Phenoxyethanol (52%), Caprylyl Glycol (42%), Sorbic Acid (6%) | 0.500% | 0.260% 0.210% 0.030% |
| Rodol Gray HED (primary dye intermediate) | N,N-Bis(2-Hydroxyethyl)-p-Phenylenediamine Sulfate | 1.800% | 1.800% |
| Benzenetriol Premix (dye coupler) | 1,2,4-Trihydroxybenzene (20%) Acetic Acid (28.57%) Sulfuric Acid (1.3%) Water (50.13) | 4.500% | 0.900% 2.786*% 0.142**% 2.255% |
| Lipo Melanin C (pigment) | Melanin (10%) Pentylene Glycol (90%) | 0.001% | 0.0001% 0.0009% |
| | TOTAL | 100.000% | 100.000% |

*as Acetamide MEA
**as Aminoethyl Sulfate

Example 4: Air Oxidation Haircolor Shampoo Composition (with Opacifier)

An air oxidation haircolor shampoo composition with opacifier was prepared using the ingredients set forth in Table 4 below.

TABLE 4

| TRADE NAME and function | INCI NAME | % WT/WT | % ACTIVE |
|---|---|---|---|
| Water, Deionized (solvent) | Water | 70.219% | 87.220% |
| FCC Kosher Erythorbic Acid (antioxidant) | Erythorbic Acid | 0.300% | 0.300% |
| Anhydrous Food Grade Sodium Sulfite (antioxidant) | Sodium Sulfite | 0.300% | 0.300% |
| Dequest 2010 (chelating agent) | Etidronic Acid | 0.030% | 0.030% |
| Mackam CBS 50G (surfactant) | Cocamidopropyl Hydroxysultaine (40%) | 2.000% | 0.800% |
| Mackanate LO (surfactant) | Disodium Lauryl Sulfosuccinate (40%) | 9.000% | 3.600% |
| Jaguar C13S (thickener & conditioner) | Guar Hydroxypropyltrimonium Chloride | 1.000% | 1.000% |
| Cerasynt IP (opacifier) | Glycol Stearate and Stearamide AMP | 2.000% | 2.000% |
| Plantaren 2000 (surfactant) | Decyl Glucoside (50%) | 5.000% | 2.500% |
| Montanov 68 (thickener) | Cetearyl Alcohol (80%) & Cetearyl Glucoside (20%) | 2.500% | 2.000% 0.500% |
| Belle Aire "Cool Water" Type OM# 88813 (olfactory enhancement) | Fragrance | 0.750% | 0.750% |
| Monoethanolamine Technical Grade (alkalizer) | Ethanolamine | 1.400% | 0.351% Free amine remaining |
| DL Panthenol (humectant & conditioner) | Panthenol | 0.100% | 0.100% |

TABLE 4-continued

| INGREDIENTS | | | |
|---|---|---|---|
| TRADE NAME and function | INCI NAME | % WT/WT | % ACTIVE |
| Manganese Sulfate Monohydrate (catalyst) | Manganese Sulfate | 0.200% | 0.200% |
| Optiphen Plus (preservative) | Phenoxyethanol (52%), Caprylyl Glycol (42%), Sorbic Acid (6%) | 0.500% | 0.260% 0.210% 0.030% |
| Rodol P Base (primary dye intermediate) | p-Aminophenol | 0.100% | 0.100% |
| Rodol Gray HED (primary dye intermediate) | N,N-Bis(2-Hydroxyethyl)-p-Phenylenediamine Sulfate | 1.100% | 1.100% |
| Benzenetriol Premix (dye coupler) | 1,2,4-Trihydroxybenzene (20%) Acetic Acid (28.57%) Sulfuric Acid (1.3%) Water (50.13) | 3.500% | 0.700% 2.167*% 0.110**% 1.754% |
| Lipo Melanin C (pigment) | Melanin (10%) Pentylene Glycol (90%) | 0.001% | 0.0001% 0.0009% |
| | TOTAL | 100.000% | 100.000% |

*as Acetamide MEA
**as Aminoethyl Sulfate

Example 5: Air Oxidation Haircolor Shampoo Composition (Creamy)

A creamy air oxidation haircolor shampoo composition was prepared using the ingredients set forth in Table 5 below.

TABLE 5

| INGREDIENTS | | | |
|---|---|---|---|
| TRADE NAME and function | INCI NAME | % WT/WT | % ACTIVE |
| Water, Deionized (solvent) | Water | 68.019% | 86.620% |
| FCC Kosher Erythorbic Acid (antioxidant) | Erythorbic Acid | 0.300% | 0.300% |
| Anhydrous Food Grade Sodium Sulfite (antioxidant) | Sodium Sulfite | 0.300% | 0.300% |
| Dequest 2010 (chelating agent) | Etidronic Acid | 0.030% | 0.030% |
| Mackam CBS 50G (surfactant) | Cocamidopropyl Hydroxysultaine (40%) | 2.000% | 0.800% |
| Mackanate LO (surfactant) | Disodium Lauryl Sulfosuccinate (40%) | 7.000% | 2.800% |
| Jaguar C13S (thickener & conditioner) | Guar Hydroxypropyltrimonium Chloride | 0.700% | 0.700% |
| Hostapon SCI 85 C (surfactant) | Sodium Cocoyl Isethionate (85%) | 2.000% | 1.700% |
| Glycerox HE (emulsifier) | PEG-7 Glyceryl Cocoate | 2.000% | 2.000% |
| Plantaren 2000 (surfactant) | Decyl Glucoside (50%) | 5.000% | 2.500% |
| Emulgade 1000 Ni (thickener) | Cetearyl Alcohol (80%) & Ceteareth-20 (20%) | 5.000% | 4.000% 1.000% |
| Belle Aire "Cool Water" Type OM# 88813 (olfactory enhancement) | Fragrance | 0.750% | 0.750% |
| Monoethanolamine Technical Grade (alkalizer) | Ethanolamine | 1.400% | 0.351% Free amine remaining |
| DL Panthenol (humectant & conditioner) | Panthenol | 0.100% | 0.100% |
| Manganese Sulfate Monohydrate (catalyst) | Manganese Sulfate | 0.200% | 0.200% |
| Optiphen Plus (preservative) | Phenoxyethanol (52%), Caprylyl Glycol (42%), Sorbic Acid (6%) | 0.500% | 0.260% 0.210% 0.030% |
| Rodol P Base (primary dye intermediate) | p-Aminophenol | 0.100% | 0.100% |
| Rodol Gray HED (primary dye intermediate) | N,N-Bis(2-Hydroxyethyl)-p-Phenylenediamine Sulfate | 1.100% | 1.100% |
| Benzenetriol Premix (dye coupler) | 1,2,4-Trihydroxybenzene (20%) Acetic Acid (28.57%) Sulfuric Acid (1.3%) Water (50.13) | 3.500% | 0.700% 2.167*% 0.110**% 1.754% |

TABLE 5-continued

| INGREDIENTS | | | |
|---|---|---|---|
| TRADE NAME and function | INCI NAME | % WT/WT | % ACTIVE |
| Lipo Melanin C (pigment) | Melanin (10%) | 0.001% | 0.0001% |
| | Pentylene Glycol (90%) | | 0.0009% |
| | TOTAL | 100.000% | 100.000% |

*as Acetamide MEA
**as Aminoethyl Sulfate

Example 6: Air Oxidation Haircolor Shampoo Composition (Anti-Dandruff)

An anti-dandruff air oxidation haircolor shampoo composition was prepared using the ingredients set forth in Table 6 below.

TABLE 6

| INGREDIENTS | | | |
|---|---|---|---|
| TRADE NAME and function | INCI NAME | % WT/WT | % ACTIVE |
| Water, Deionized (solvent) | Water | 68.309% | 86.447% |
| FCC Kosher Erythorbic Acid (antioxidant) | Erythorbic Acid | 0.300% | 0.300% |
| Anhydrous Food Grade Sodium Sulfite (antioxidant) | Sodium Sulfite | 0.300% | 0.300% |
| Mackam CBS 50G (surfactant) | Cocamidopropyl Hydroxysultaine (40%) | 2.000% | 0.800% |
| Mackanate LO (surfactant) | Disodium Lauryl Sulfosuccinate (40%) | 9.000% | 3.600% |
| Jaguar C13S (thickener & conditioner) | Guar Hydroxypropyltrimonium Chloride | 1.000% | 1.000% |
| Cerasynt IP (opacifier) | Glycol Stearate and Stearamide AMP | 2.000% | 2.000% |
| Plantaren 2000 (surfactant) | Decyl Glucoside (50%) | 5.000% | 2.500% |
| Montanov 68 (thickener) | Cetearyl Alcohol (80%) & | 2.500% | 2.000% |
| | Cetearyl Glucoside (20%) | | 0.500% |
| Belle Aire "Cool Water" Type OM# 88813 (olfactory enhancement) | Fragrance | 0.750% | 0.750% |
| Monoethanolamine Technical Grade (alkalizer) | Ethanolamine | 1.450% | 0.401% Free amine remaining |
| DL Panthenol (humectant & conditioner) | Panthenol | 0.100% | 0.100% |
| Zinc Omadine 48% dispersion (anti-dandruff active) | Zinc Pyrithione | 2.090% | 1.003% |
| Optiphen Plus (preservative) | Phenoxyethanol (52%), | 0.500% | 0.260% |
| | Caprylyl Glycol (42%), | | 0.210% |
| | Sorbic Acid (6%) | | 0.030% |
| Rodol P Base (primary dye intermediate) | p-Aminophenol | 0.100% | 0.100% |
| Rodol Gray HED (primary dye intermediate) | N,N-Bis(2-Hydroxyethyl)-p-Phenylenediamine Sulfate | 1.100% | 1.100% |
| Benzenetriol Premix (dye coupler) | 1,2,4-Trihydroxybenzene (20%) | 3.500% | 0.700% |
| | Acetic Acid (28.57%) | | 2.167*% |
| | Sulfuric Acid (1.3%) | | 0.110**% |
| | Water (50.13) | | 1.754% |
| Lipo Melanin C (pigment) | Melanin (10%) | 0.001% | 0.0001% |
| | Pentylene Glycol (90%) | | 0.0009% |
| | TOTAL | 100.000% | 100.000% |

*as Acetamide MEA
**as Aminoethyl Sulfate

Example 7: Air Oxidation Haircolor Cleanser Composition

An air oxidation haircolor cleanser composition was prepared using the ingredients set forth in Table 7 below. Specifically, this air oxidation haircolor cleanser composition is formulated with less surfactant to produce less lather for use as a facial cleanser and to dye facial hair.

TABLE 7

INGREDIENTS

| TRADE NAME and function | INCI NAME | % WT/WT | % ACTIVE |
|---|---|---|---|
| Water, Deionized (solvent) | Water | 70.899% | 86.700% |
| FCC Kosher Erythorbic Acid (antioxidant) | Erythorbic Acid | 0.200% | 0.200% |
| Anhydrous Food Grade Sodium Sulfite (antioxidant) | Sodium Sulfite | 0.300% | 0.300% |
| Dequest 2010 (chelating agent) | Etidronic Acid | 0.100% | 0.100% |
| Emulgade 1000 Ni (thickener) | Cetearyl Alcohol (80%) & Ceteareth-20 (20%) | 5.000% | 4.000% 1.000% |
| Glycerox HE (emulsifier) | PEG-7 Glyceryl Cocoate | 3.000% | 3.000% |
| Incroquat Behenyl TMS (conditioner) | Behentrimonium Methosulfate (25%) & Cetearyl Alcohol (75%) | 2.700% | 0.675% 2.025% |
| Dow Corning 200 fluid (conditioner) | Dimethicone | 4.000% | 4.000% |
| Brij 721 (emulsifier) | Steareth-21 | 0.500% | 0.500% |
| Mackam CBS-50G (surfactant) | Cocamidopropyl Hydroxysultaine | 5.000% | 2.000% |
| Hostapon SCI 85 C (surfactant) | Sodium Cocoyl Isethionate (85%) | 2.000% | 1.700% |
| Belle Aire "Cool Water" Type OM# 88813 (olfactory enhancement) | Fragrance | 0.500% | 0.500% |
| Monoethanolamine Technical Grade (alkalizer) | Ethanolamine | 1.300% | 0.380% free amine remaining |
| Rodol P Base (primary dye intermediate) | p-Aminophenol | 0.100% | 0.100% |
| Manganese Sulfate Monohydrate (catalyst) | Manganese Sulfate | 0.200% | 0.200% |
| Neolone PE (preservative) | Methylisothiazolinone (2.0%) & Phenoxyethanol (85%) & Propanediol (13%) | 0.500% | 0.010% 0.425% 0.065% |
| Rodol Gray HED (primary dye intermediate) | N,N-Bis(2-Hydroxyethyl)-p-Phenylenediamine Sulfate | 0.700% | 0.700% |
| Benzenetriol Premix (dye coupler) | 1,2,4-Trihydroxybenzene (20%) Acetic Acid (28.57%) Sulfuric Acid (1.3%) Water (50.13) | 3.000% | 0.600% 1.728*% 0.088**% 1.504% |
| Lipo Melanin C (pigment) | Melanin (10%) Pentylene Glycol (90%) | 0.001% | 0.0001% 0.0009% |
| | TOTAL | 100.000% | 100.000% |

Comparative Example

Table 8 includes a list of compositions, with Examples 8, 9, 11 and 12 being air oxidation haircolor compositions of the present disclosure. The formulas were dyed out on 90% gray hair (supplied by IHIP) with a 1 minute dwell time, followed by rinsing with water and blow drying. This process was repeated over a 10 day period, by repeating the process one time per day. After each treatment, color measurements were recorded using an X-Rite XTH spectrophotometer and the Hunter L.a.b. scale. This data is presented in Table 9.

TABLE 8

Hair Care Compositions

| Ingredients | Example 8: Air Oxidation Haircolor Shampoo Composition WT % | Example 9: Air Oxidation Haircolor Catalyzed Shampoo Composition WT % | Example 10: Comparative Example WT % | Example 11: Air Oxidation Haircolor Conditioner Composition WT % | Example 12: Air Oxidation Haircolor Composition Catalyzed Rinse-off WT % |
|---|---|---|---|---|---|
| D.I. Water | 81.700 | 81.500 | 81.700 | 84.310 | 83.550 |
| Manganese Sulfate | | 0.200 | | | 0.100 |
| Etidronic Acid | 0.050 | 0.050 | 0.050 | | 0.100 |
| Disodium EDTA | | | | 0.050 | |
| Erythorbic Acid | 0.050 | 0.050 | 0.050 | 0.020 | 0.150 |
| Sodium Sulfite | 0.050 | 0.050 | 0.050 | 0.020 | 0.100 |
| Cocamiopropyl Hydroxysultaine (recorded as active level) | | | | | 2.000 |
| Sodium Cocyl Isethionate (recorded as active level) | | | | | 2.000 |
| Sodium Laureth Sulfate (recorded as active level) | 5.000 | 5.000 | 5.000 | | |
| Cetearyl Alcohol (65%) & Ceteth-20 Phosphate (15%) & Dicetyl Phosphate (20%) | | | | 1.000 | |
| Cocamidopropylamine Oxide | 1.000 | 1.000 | 1.000 | | |
| Disodium Lauryl Sulfosuccinate (recorded as active level) | | | | | |
| Decyl Glucoside (recorded as active level) | 3.000 | 3.000 | 3.000 | | |
| Sodium Lauryl Sarcosinate (recorded as active level) | 5.000 | 5.000 | 5.000 | | |
| Hydroxyethyl Cellulose | | | | 0.200 | |
| Guar Hydroxypropyltrimonium Chloride | 1.000 | 1.000 | 1.000 | | |
| Cetearyl Alcohol & Ceteareth -20 | | | | 5.000 | 6.000 |
| Laureth-23 | | | | 1.000 | 2.000 |
| Behentrimonium Methosulfate & Cetearyl Alcohol | | | | 3.000 | 1.000 |
| Polyquaternium-22 | | | | | 1.000 |
| Dimethicone | | | | 3.000 | |
| Aminomethyl Propanol | 0.500 | 0.500 | 0.500 | | |
| Triethanolamine | | | | 1.000 | |
| Monoethanolamine | | | | | 0.200 |
| 1,2,4-Trihydroxybenzene | 1.000 | 1.000 | | 0.500 | 1.000 |
| p-Phenylenediamine | 0.100 | 0.100 | 0.100 | | |
| p-Toluenediamine | | | | | 0.200 |
| p-Aminophenol | 0.050 | 0.050 | 0.050 | 0.100 | 0.500 |
| N,N-Bis(2-Hydroxyethyl)-p-Phenylenediamine Sulfate | 1.500 | 1.500 | 1.500 | 0.800 | |
| 2,4-Diaminophenoxy ethanol sulfate | | | | | 0.100 |
| m-Aminophenol | | | 1.000 | | |
| pH | 6.7 | 6.8 | 6.8 | 7.3 | 7.4 |

TABLE 9

| Treatments | | Example 8 | Example 9 | Example 10 | Example 11 | Example 12 |
|---|---|---|---|---|---|---|
| Color Measurement | | | | | | |
| Untreated 90% gray hair | | L = 58.1<br>a = 0.1<br>b = 11.0 | L = 56.7<br>a = 0.5<br>b = 11.1 | L = 58.3<br>a = 0.2<br>b = 11.4 | L = 58.9<br>a = 0.9<br>b = 11.8 | L = 56.2<br>a = 0.5<br>b = 10.7 |
| 1 treatment | | L = 39.8<br>a = 1.6<br>b = 6.9 | L = 38.1<br>a = 1.7<br>b = 6.3 | L = 55.6<br>a = 1.1<br>b = 11.9 | L = 42.3<br>a = 2.1<br>b = 8.1 | L = 43.1<br>a = 2.8<br>b = 9.6 |
| 2 treatments | | L = 34.7<br>a = 2.0<br>b = 6.0 | L = 33.3<br>a = 1.6<br>b = 5.8 | L = 52.0<br>a = 1.2<br>b = 11.8 | L = 32.5<br>a = 2.0<br>b = 7.0 | L = 36.9<br>a = 2.6<br>b = 9.9 |
| 3 treatments | | L = 31.8<br>a = 1.6<br>b = 5.0 | L = 30.1<br>a = 1.3<br>b = 5.1 | L = 50.3<br>a = 1.2<br>b = 11.5 | L = 29.3<br>a = 1.4<br>b = 6.1 | L = 28.8<br>a = 2.7<br>b = 8.2 |
| 4 treatments | | L = 27.0<br>a = 1.4<br>b = 4.3 | L = 25.6<br>a = 1.2<br>b = 4.4 | L = 48.3<br>a = 1.1<br>b = 10.6 | L = 27.5<br>a = 1.2<br>b = 5.4 | L = 25.8<br>a = 2.6<br>b = 7.3 |
| 5 treatments | | L = 24.8<br>a = 1.4<br>b = 4.2 | L = 23.2<br>a = 0.9<br>b = 3.7 | L = 44.9<br>a = 0.8<br>b = 9.2 | L = 23.2<br>a = 1.2<br>b = 4.6 | L = 24.4<br>a = 2.6<br>b = 6.8 |
| 6 treatments | | L = 24.5<br>a = 1.3<br>b = 3.7 | L = 22.0<br>a = 1.1<br>b = 3.9 | L = 44.7<br>a = 1.1<br>b = 9.6 | L = 21.7<br>a = 1.2<br>b = 3.9 | L = 23.7<br>a = 2.6<br>b = 6.4 |
| 7 treatments | | L = 21.8<br>a = 1.4<br>b = 3.6 | L = 20.2<br>a = 1.1<br>b = 3.2 | L = 43.3<br>a = 1.0<br>b = 9.1 | L = 20.7<br>a = 1.0<br>b = 3.5 | L = 21.2<br>a = 2.5<br>b = 5.3 |
| 8 treatments | | L = 20.7<br>a = 1.2<br>b = 3.4 | L = 19.3<br>a = 0.9<br>b = 3.0 | L = 39.3<br>a = 1.0<br>b = 7.7 | L = 20.1<br>a = 0.9<br>b = 3.3 | L = 20.6<br>a = 2.3<br>b = 4.5 |
| 9 treatments | | L = 19.2<br>a = 1.2<br>b = 3.0 | L = 18.1<br>a = 0.9<br>b = 2.6 | L = 37.6<br>a = 1.2<br>b = 7.5 | L = 18.3<br>a = 0.8<br>b = 2.7 | L = 18.7<br>a = 2.0<br>b = 3.3 |
| 10 treatments | | L = 18.8<br>a = 1.2<br>b = 2.7 | L = 16.8<br>a = 0.9<br>b = 2.5 | L = 36.6<br>a = 1.6<br>b = 7.7 | L = 16.9<br>a = 0.9<br>b = 2.5 | L = 18.5<br>a = 2.2<br>b = 3.5 |

"L" = lightness, + is lighter and − is darker.
"a" = relative amounts of red and green, + is more red and − is greener.
"b" = relative amounts of yellow and blue, + is more yellow and − is bluer.

As shown by a review of the data in Table 9, use of a transition metal salt as a haircolor catalyst, as in Example 9, aids in the deposition of color given the short dwell times. Examples 8 and 9 in Table 8 are identical, except that Example 9 includes manganese sulfate as a catalyst. Manganese ions ($MN^{++}$) are a preferred catalyst to enhance color delivery. Additionally, any build-up of manganese in the hair does not adversely affect the physical condition of the hair, as can be the case with the use of iron or copper ions. The increase in color delivery is demonstrated by the lower "L" values recorded for Example 9 as compared to the values for Example 8.

As mentioned above, a preferred aromatic triol is 1,2,4-trihydroxybenzene. As shown in Table 8, Example 10 is formulated using a conventional oxidation dye coupler, m-Aminophenol, instead of 1,2,4-trihydroxybenzene. Example 10 is identical to Example 8, except that 1,2,4-trihydroxybenzene was replaced with an equal amount of m-Aminophenol. The decrease in color delivery for Example 10 compared to Example 8 is indicated by the higher "L" values recorded in Table 9.

While the disclosure has been described above with reference to specific embodiments thereof, it is apparent that many changes, modifications, and variations can be made without departing from the concept disclosed herein. Accordingly, it is intended to embrace all such changes, modifications, and variations that fall within the spirit and broad scope of the appended claims.

What is claimed is:

1. A method for gradually coloring hair comprising the steps of:
    a) applying an air oxidation haircolor composition to hair;
    b) removing the air oxidation haircolor composition from the hair directly after application; and
    c) repeating a set comprising the steps a) and b) in multiple spaced intervals,
    wherein the air oxidation haircolor composition comprises a lamellar phase.

2. The method of claim 1, wherein the air oxidation haircolor composition is applied at least once per week.

3. The method of claim 1, wherein the air oxidation haircolor composition is applied at least once daily.

4. The method of claim 1, wherein the air oxidation haircolor composition is removed from the hair within 1 to 10 minutes after application.

5. The method of claim 1, wherein the step of removing the air oxidation haircolor composition is performed within 15 minutes after application.

6. The method of claim 1, wherein the air oxidation haircolor composition comprises at least one cleansing surfactant.

7. The method of claim 1, wherein the air oxidation haircolor composition comprises the at least one conditioning agent.

8. The method of claim 6, wherein the air oxidation haircolor composition further comprises at least one conditioning agent.

9. The method of claim 6, wherein the set comprising the steps a) and b) simultaneously cleanses and gradually colors the hair, and wherein the air oxidation haircolor composition is an air oxidation haircolor shampoo composition.

10. The method of claim 8, wherein the set comprising the steps a) and b) simultaneously cleanses, conditions, and gradually colors the hair, and wherein the air oxidation haircolor composition is an air oxidation haircolor shampoo and conditioning composition.

11. The method of claim 1, wherein the air oxidation haircolor composition further comprises:
   at least one primary oxidation dye intermediate;
   at least one aromatic triol; and
   water.

12. The method of claim 11, wherein a primary oxidation dye intermediate content in the air oxidation haircolor composition is about 0.1% to about 3% weight by weight, an aromatic triol content in the air oxidation haircolor composition is about 0.1% to about 3% weight by weight, and a water content in the air oxidation haircolor composition is about 40% to about 98% weight by weight.

13. The method of claim 11, wherein the at least one aromatic triol is selected from the group consisting of: 1,2,4-benzenetriol, 2,4,5-trihydroxytoluene, pyrogallol, and any combination thereof.

14. The method of claim 13, wherein the air oxidation haircolor composition comprises 1,2,4-benzenetriol.

15. The method of claim 1, wherein at least about 80 weight % of surfactants in the air oxidation haircolor composition can form bilayers.

16. The composition of claim 6, wherein the at least one cleansing surfactant is an anionic, an amphoteric, or a nonionic cleansing surfactant.

17. The method of claim 6, wherein the at least one cleansing surfactant comprises:
   at least one anionic cleansing surfactant selected from the group consisting of at least one sulfosuccinate and at least one isethionate;
   at least one sultaine;
   at least one alkyl poly glucoside; and
   at least one fatty derivative.

18. The method of claim 1, wherein the air oxidation haircolor composition comprises at least one anti-dandruff agent.

* * * * *